(12) United States Patent
Chang et al.

(10) Patent No.: US 8,134,865 B2
(45) Date of Patent: Mar. 13, 2012

(54) OPERATING METHOD OF ELECTRICAL PULSE VOLTAGE FOR RRAM APPLICATION

(75) Inventors: Kuo-Pin Chang, Yuanli Township (TW);
Yi-Chou Chen, Hsinchu (TW);
Wei-Chih Chien, Sijhih (TW);
Erh-Kun Lai, Elmsford, NY (US)

(73) Assignee: Macronix International Co., Ltd., Hsinchu (TW)

( * ) Notice: Subject to any disclaimer, the term of this patent is extended or adjusted under 35 U.S.C. 154(b) by 487 days.

(21) Appl. No.: 12/366,949

(22) Filed: Feb. 6, 2009

(65) Prior Publication Data

US 2009/0279343 A1 Nov. 12, 2009

Related U.S. Application Data

(60) Provisional application No. 61/050,774, filed on May 6, 2008.

(51) Int. Cl.
*G11C 11/00* (2006.01)
(52) U.S. Cl. ........................... 365/163; 365/148; 365/153
(58) Field of Classification Search .................. 365/163, 365/148, 153
See application file for complete search history.

(56) References Cited

U.S. PATENT DOCUMENTS

| | | | | |
|---|---|---|---|---|
| 6,072,716 | A * | 6/2000 | Jacobson et al. | 365/163 |
| 6,914,255 | B2 * | 7/2005 | Lowrey | 257/5 |
| 7,292,469 | B2 | 11/2007 | Lee et al. | |
| 2005/0270821 | A1 | 12/2005 | Nakano | |
| 2007/0159869 | A1 * | 7/2007 | Baek et al. | 365/148 |
| 2007/0215977 | A1 | 9/2007 | Lee et al. | |
| 2007/0267675 | A1 | 11/2007 | Cho et al. | |
| 2008/0013363 | A1 | 1/2008 | Kim et al. | |
| 2008/0062740 | A1 | 3/2008 | Baek et al. | |
| 2008/0304312 | A1 | 12/2008 | Ho et al. | |

OTHER PUBLICATIONS

Baik I.G., et al., "Highly Scalable Non-volatile Resistive Memory using Simple Binary Oxide Driven by Asymmetric Unipolar Voltage Pulses," IEEE IEDM 2004, 4 pages.
Ho, Chiahua, et al., "A Highly Reliable Self-Aligned Graded Oxide $Wo_x$ Resistance Memory: Conduction Mechanisms and Reliability," 2007 Symp. on VLSI Technology Digest of Technical Papers, 228-229.
Lin, Chih-Yang, et al., "Bistable Resistive Switching in $Al_2O_3$ Memory Thin Films," J. Electrochem. Soc., 154(9) Jul. 9, 2007, 4 pages.
Lin, Chih-Yang, et al., "Effect of Top Electrode Material on Resistive Switching Properties of $ZrO_2$ Film Memory Devices," IEEE Electron Device Letters, vol. 28, No. 5, May 2007, 3 pages.
Lv, H.B., et al., "Forming Process Investigation of $Cu_xO$ Memory Films," IEEE Electron Device Letters, vol. 29, No. 1, Jan. 2008, 3 pages.
Yoshida, Chikako, et al., "High speed resistive switching in $Pt/TiO_2/TiN$ film for nonvolatile memory application," Appl. Phys. Lett. 91, 2007, 3 pages.
You, Yil-Hwan, et al., "Impedance spectroscopy characterization of resistance switching NiO thin films prepared through atomic layer deposition," Appl. Phys. Lett. 89, 2006, 3 pages.

* cited by examiner

*Primary Examiner* — Son Dinh
(74) *Attorney, Agent, or Firm* — Haynes Beffel & Wolfeld LLP

(57) ABSTRACT

Metal-oxide based memory devices and methods for operating and manufacturing such devices are described herein. A method for manufacturing a memory device as described herein comprises forming a metal-oxide memory element, and applying an activating energy to the metal-oxide memory element. In embodiments the activating energy can be applied by applying electrical and/or thermal energy to the metal-oxide material.

31 Claims, 18 Drawing Sheets

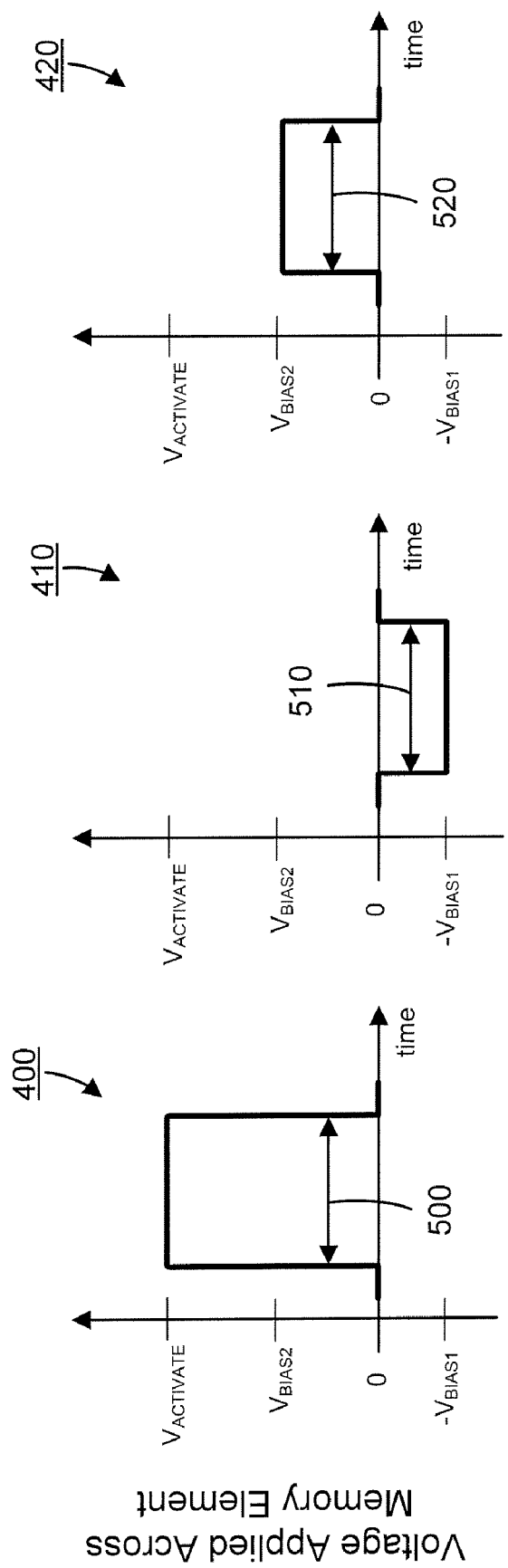

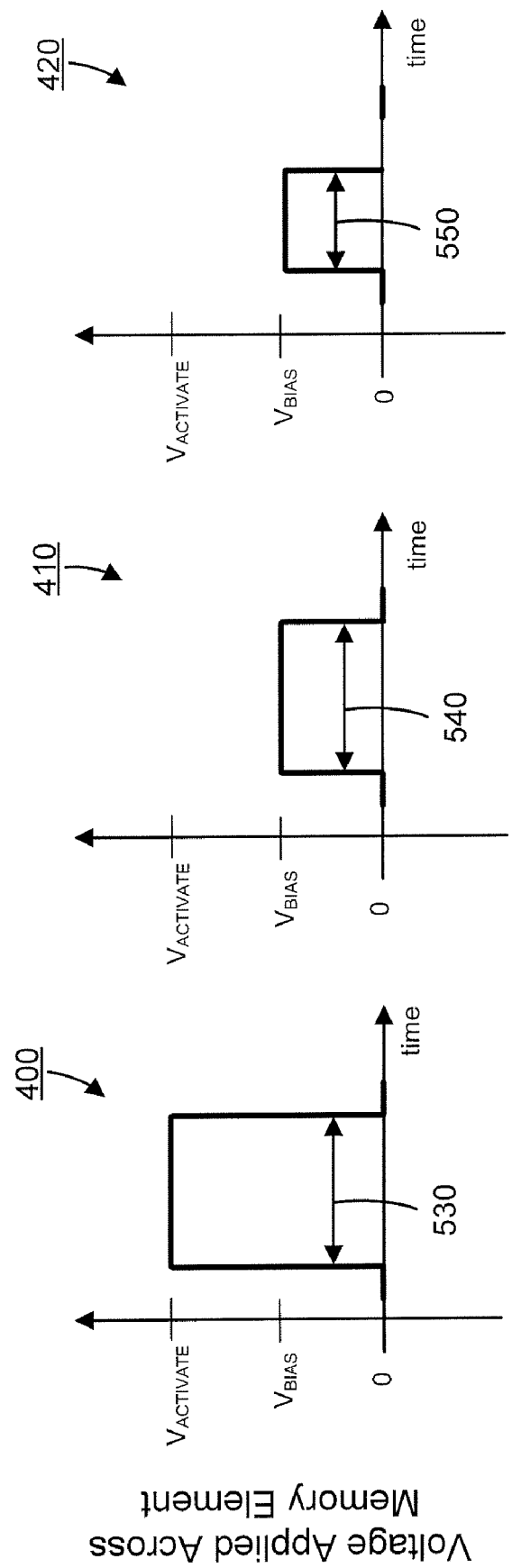

V=3, R is about 5 k ohm

V=3, R is about 12 k ohm

OPERATING METHOD OF ELECTRICAL PULSE VOLTAGE FOR RRAM APPLICATION

CROSS-REFERENCE TO RELATED APPLICATIONS

This application claims the benefit of U.S. Provisional Patent Application No. 61/050,774 titled "Operation Method of Electrical Pulse Voltage for RRAM Application" filed on 6 May 2008, which is incorporated by reference herein.

BACKGROUND OF THE INVENTION

1. Field of the Invention

The present invention relates to metal-oxide based memory devices and methods for operating and manufacturing such devices.

2. Description of Related Art

Some metal-oxides can be caused to change resistance between two or more stable resistance ranges by application of electrical pulses at levels suitable for implementation in integrated circuits, thus providing a basis for use in nonvolatile resistive random access memory RRAM. Metal-oxide based RRAM has attracted much attention because of its simple structure, high speed, low power consumption, and compatibility with standard CMOS processes.

In metal-oxide based memory, data is stored by applying energy pulses to the metal-oxide material to induce a change in resistance of the metal-oxide material between two or more resistance states. Multi-bit operation involves changing the resistance of the metal-oxide material between more than two resistance states and is desirable since the data storage density can be increased and the process costs can be reduced.

It has been reported that some metal-oxides require a "forming process" to cause a breakdown from a high resistance state to a low resistance state in order to enable the resistive switching behavior of the material. As illustrated in FIG. 1, the forming process typically involves increasing a DC voltage applied across the metal-oxide material until breakdown from a high resistance state to a low resistance state is achieved. The forming process occurs at a forming voltage ($V_{forming}$) which is often much larger than the magnitudes of a set pulse ($V_{set}$) and a reset pulse ($V_{reset}$) which are then applied to induce a resistive state change in the metal-oxide material. The relatively large forming voltage ($V_{forming}$) increases the complexity of the circuitry of memory devices employing these types of metal-oxide materials. Additionally, the forming process of sweeping the DC voltage takes a relatively large time (for example greater than 60 µs), which increases the test time of the device significantly. The table below summarizes the reported forming voltage for various metal-oxides.

| Metal Oxide | Forming Voltage |
|---|---|
| $NiO_x$ | 8.1 V |
| $TiO_2$ | 5 V |
| $CuO_x$ | 16.5 V |
| $ZrO_2$ | 8.8 V |
| $Al_2O_3$ | 11 V |

Tungsten-oxide $WO_x$ based RRAM has been shown to exhibit good resistive switching characteristics between two or more resistance ranges without the need for a forming process. See, U.S. patent application Ser. No. 11/955,137 (now U.S. Patent Publication No. 2008/0304312) entitled "Memory Devices Having an Embedded Resistance Memory with Tungsten Compound and Manufacturing Methods", filed 12 Dec. 2007 and incorporated by reference herein.

In order to reliably distinguish between the various resistance states, and thus properly determine the data value stored in a memory cell, it is important to maintain relatively large resistance windows between the states. Additionally, it is important to maintain a large resistance window between the highest and lowest resistance states used to represent data in order to provide an opportunity to achieve multi-bit operation.

Previous attempts for increasing the resistance window between the highest and lowest resistance states involves increasing the voltage magnitude of a reset pulse applied across the metal-oxide material. However, endurance problems have arisen using large magnitude reset pulses due to instability of the resistance of the metal-oxide material, resulting in reliability issues and possible failure of the device.

It is therefore desirable to provide metal-oxide based memory devices and methods for manufacturing and operating such devices which address the endurance problems discussed above and result in improved reliability and data storage performance of the device.

SUMMARY OF THE INVENTION

A method for manufacturing a memory device as described herein comprises forming a metal-oxide memory element, and applying an activating energy to the metal-oxide memory element. In embodiments the activating energy can be applied by applying electrical and/or thermal energy to the metal-oxide material. Unlike the forming process of FIG. 1 in which high resistance material is formed to a lower resistance state in order to enable the resistive switching behavior, the activating energy described herein can remove leakage paths inside the metal-oxide material and result in an increase in the initial resistance of the metal-oxide material.

A memory device as described herein comprises a metal-oxide memory element programmable to a plurality of resistance states including a lower resistance state and a higher resistance state. The memory device further comprises bias circuitry adapted to apply bias arrangements across the metal-oxide memory element, the bias arrangements comprising an activating bias arrangement to apply an activating energy to the metal-oxide memory element.

Applying the activating energy as described herein is shown to result in the ability to use lower operating voltages for programming the metal-oxide memory element 140. Thus, the electrical stress on the memory element can be reduced and improved cycle endurance is observed. Additionally, applying the activating energy is shown to improve read disturbance and result in a larger resistance window between the resistance states, thereby providing an opportunity for multi-bit operation.

Other aspects and advantages of the present invention can be seen on review of the drawings, the detailed description, and the claims which follow.

BRIEF DESCRIPTION OF THE DRAWINGS

FIGS. 4 and 5A-5C conceptually illustrate the resistive state change behavior of metal-oxide memory element along with an embodiment of applying an activating bias arrangement as described herein.

FIGS. 5D-5F illustrate a second embodiment including an activating bias arrangement as described herein.

DETAILED DESCRIPTION

Figure 1:
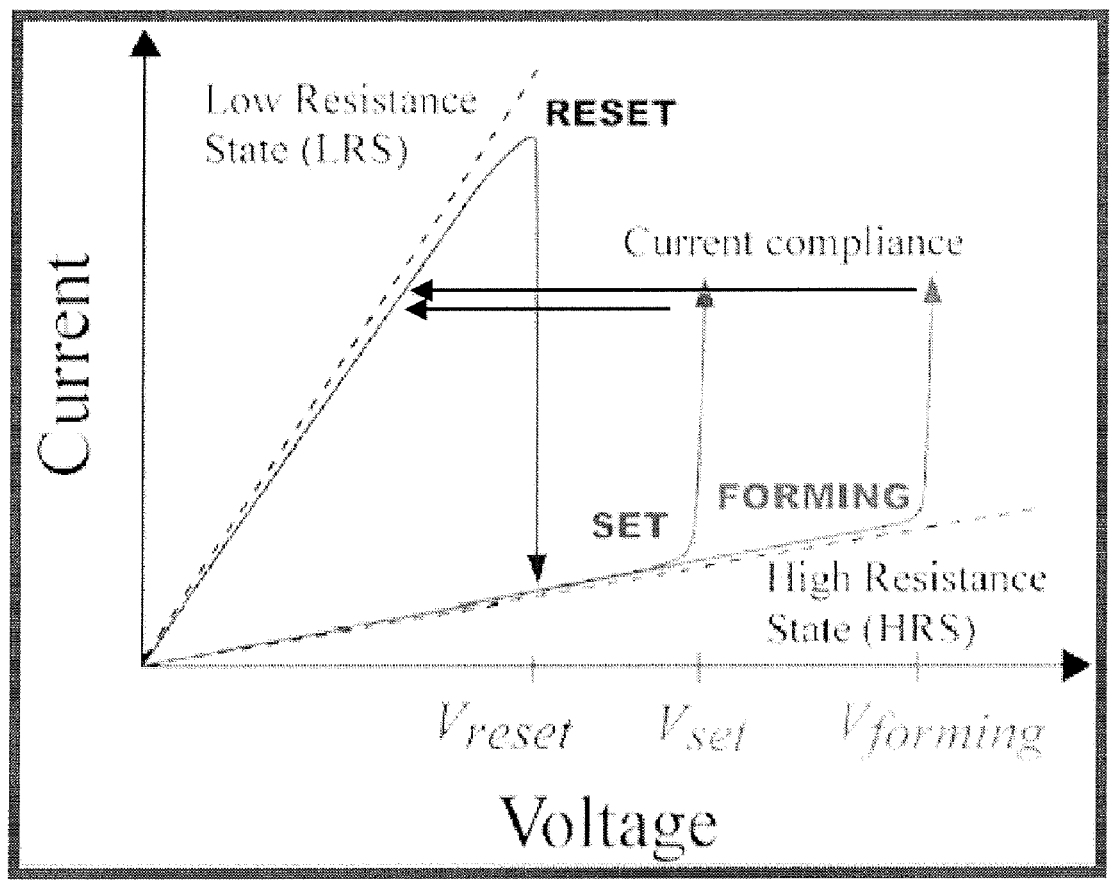
FIG. 1 illustrates a DC forming process.

The following description of the disclosure will typically be with reference to specific structural embodiments and methods. It is to be understood that there is no intention to limit the disclosure to the specifically disclosed embodiments and methods, but that the disclosure may be practiced using other features, elements, methods and embodiments. Preferred embodiments are described to illustrate the present disclosure, not to limit its scope, which is defined by the claims. Those of ordinary skill in the art will recognize a variety of equivalent variations on the description that follows. Like elements in various embodiments are commonly referred to with like reference numerals.

As described above, endurance problems have arisen using large magnitude pulses to change to the highest resistance state due to instability in the resistance of metal-oxide memory elements which reduce the resistance window between the highest and lowest resistance state, resulting in reliability issues and possible failure of the device.

Figure 2:
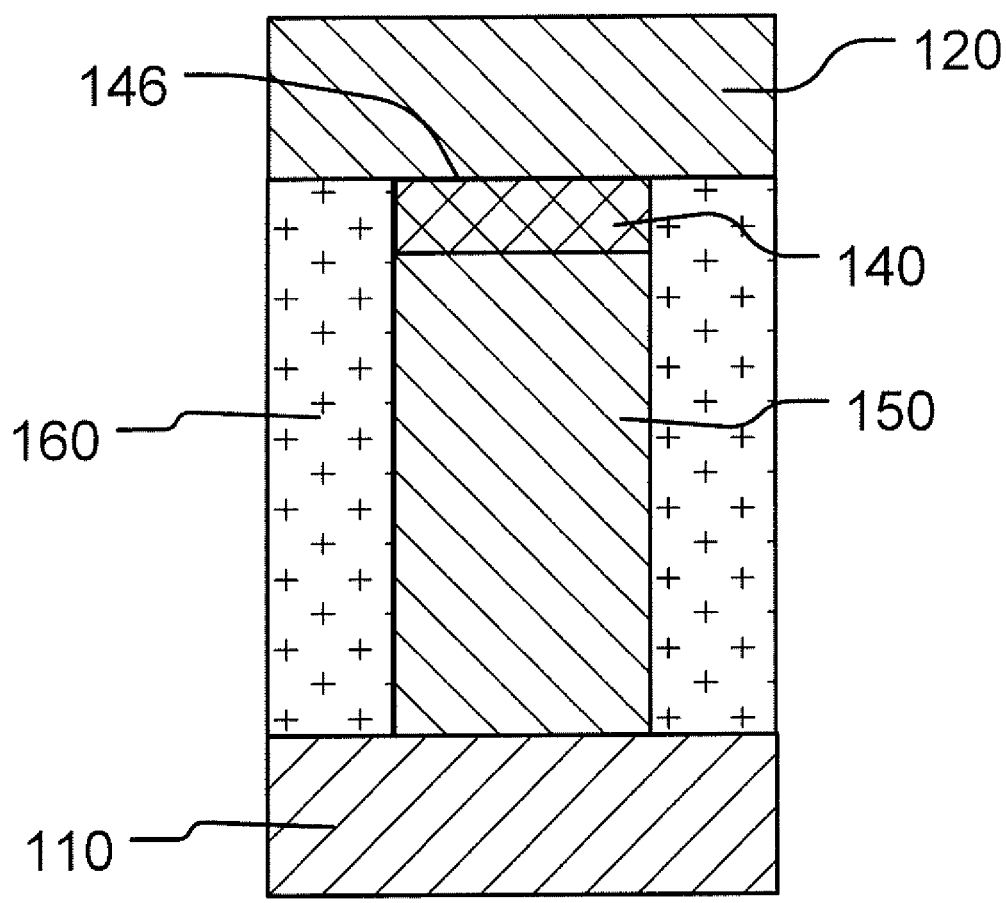
FIG. 2 illustrates a cross-sectional view of a metal-oxide based memory cell.

FIG. 2 illustrates a cross-sectional view of a metal-oxide based memory cell 100 manufactured by applying an activating energy as described herein to the metal-oxide memory element 140. As discussed in more detail below, the activating energy can be applied by applying electrical and/or thermal energy to the metal-oxide material to remove unnecessary leakage paths inside the metal-oxide material. As a result of applying the activating energy, the operating voltages needed for programming the metal-oxide memory element 140 are reduced. Thus, the electrical stress on the memory element 140 can be reduced and improved cycle endurance is observed.

The memory cell 100 includes a conductive element 150 extending through dielectric 160 to couple a bottom electrode 110 to a memory element 140. The dielectric 160 comprises silicon oxide in the illustrate embodiment, although other dielectric materials can alternatively be used.

The memory element 140 comprises at least one programmable metal-oxide, and in the illustrated embodiment the conductive element 150 comprises tungsten and the memory element 140 comprises tungsten-oxide $WO_x$. In embodiments the memory element 140 can have a variation in distribution of oxygen content of $WO_x$ compounds with depth from the top surface 146 which results in both monotonically decreasing ion valence values ($W^{+6}$, $W^{+5}$, $W^{+4}$, and $W^0$), as well as lower oxygen content in the deeper regions. In alternative embodiments the memory element may comprise other metal-oxides, for example a metal-oxide from the group of nickel oxide, aluminum oxide, magnesium oxide, cobalt oxide, titanium oxide, titanium-nickel oxide, zirconium oxide, and copper oxide.

The bottom electrode 110 is an electrically conductive element. For example, the bottom electrode 110 may be doped semiconductor material such as a terminal of an access transistor or diode. Alternatively, the bottom electrode 110 may comprise, for example, one or more elements selected from the group consisting of Ti, W, Mo, Al, Ta, Cu, Pt, It, La, Ni, N, O, and Ru and combinations thereof, and in some embodiments may comprise more than one layer.

The memory cell 100 also includes a top electrode 120 on the memory element 140. The top electrode 120 (which in some embodiments is a portion of a bit line) may comprise, for example, any of the materials discussed above with reference to the bottom electrode 110, and in some embodiments may comprise more than one layer.

The metal-oxide memory element 140 can be formed by various deposition and oxidation techniques. The memory element 140 can be formed by an oxidation process following conventional back-end-of-line W-plug process of depositing W material within a via and performing a CMP process, resulting in the memory element 140 located between the conductive element 150 and the subsequently formed material of the top electrode 120. Methods for forming the tungsten-oxide memory element 140 include direct plasma oxidation, down-stream plasma oxidation, sputtering, and reactive sputtering. Embodiments for the plasma oxidation process include a pure $O_2$ gas chemistry, or mix chemistries such as $O_2/N_2$, or $O_2/N_2/H_2$. In one embodiment of the down-stream plasma, the down-stream plasma is applied with a pressure of about 1500 mtorr, a power of about 1000 W, an $O_2/N_2$ flow of about 3000 scc/200 sccm, a temperature of about 150° C., and a time duration of about 400 seconds. See, for example, U.S. patent application Ser. No. 11/955,137 (now US Patent Publication No. 2008/0304312), which is incorporated by reference herein.

FIGS. 3A-3D illustrate cross-sectional views of steps in a process for manufacturing the memory cell 100 including applying the activating energy.

Figure 3A:
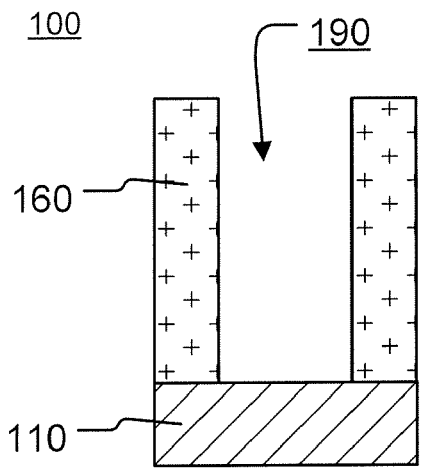
FIGS. 3A-3D illustrate cross-sectional views of steps in a process for manufacturing the memory cell of FIG. 2.

FIG. 3A illustrates a first step of forming the dielectric 160 on bottom electrode 110, and etching the dielectric 160 to form a via 190 extending through the dielectric 160 to the bottom electrode 110. In the illustrated embodiment the dielectric 160 comprises silicon dioxide, although other dielectric materials can also be used.

Figure 3B:
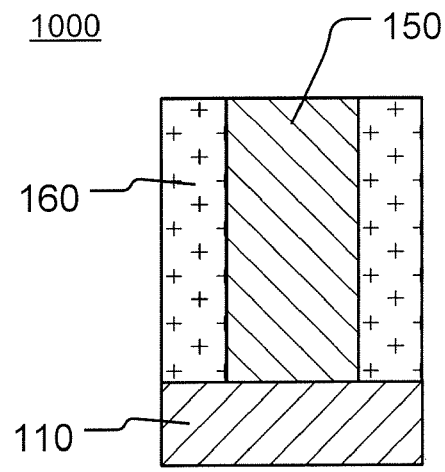

Next, conductive element 150 is formed within the via 190, resulting in the structure illustrated in the cross-sectional view of FIG. 3B. The conductive element 150 comprises tungsten material in the illustrated embodiment and can be formed within the via 190 by Chemical Vapor Deposition CVD followed by a planarization step such as Chemical Mechanical Polishing CMP.

Figure 3C:
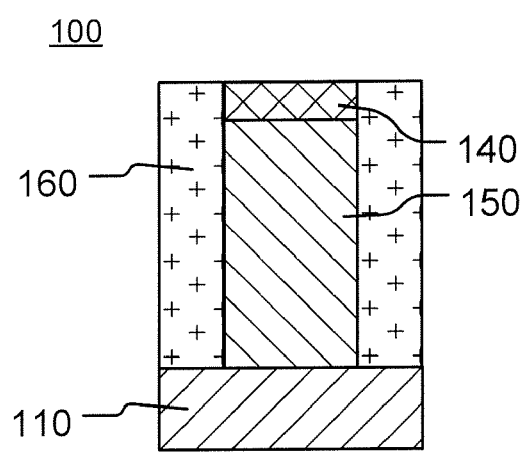
Figure 3D:
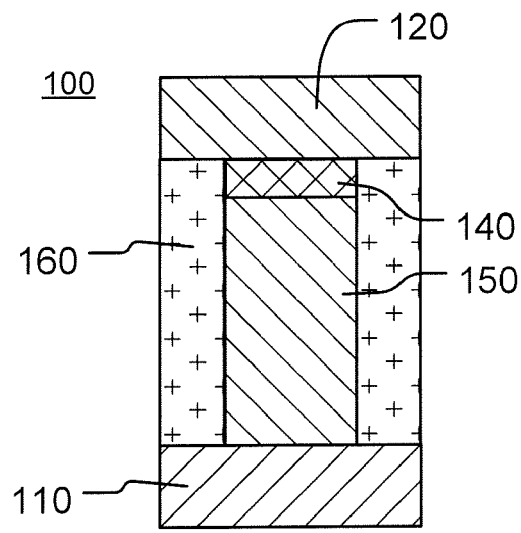

Next, oxidation of a portion of the conductive element 150 forms memory element 140 self-aligned with the remaining portion of the conductive element 150, resulting in the structure illustrated in FIG. 3C. In the illustrated embodiment the conductive element 150 comprises tungsten material, and thus the memory element 140 comprises tungsten-oxide. In alternative embodiments the memory element 140 may comprise other metal-oxides, for example a metal-oxide from the group of nickel oxide, aluminum oxide, magnesium oxide, cobalt oxide, titanium oxide, titanium-nickel oxide, zirconium oxide, and copper oxide Next, top electrode 120 is formed on the structure illustrated in FIG. 3C, resulting in the structure illustrated in the cross-sectional view of FIG. 3D.

Next, electrical and/or thermal activating energy is applied to the metal-oxide memory element 140 to remove unnecessary leakage paths inside the metal-oxide material. The results discussed herein with reference to FIGS. 4 to 15 demonstrate that applying the activating energy results in the ability to subsequently use lower energy bias arrangements for programming the metal-oxide memory element 140, which reduces the electrical stress on the memory element 140 and improves the cycle endurance. The activating energy is also shown to result in improved resistive switching performance of the metal-oxide material including improved read disturbance performance. The activating energy is also shown to result in a larger resistance window between resistance states, thereby providing an opportunity for multi-bit operation.

As discussed below with reference to FIGS. 4 to 13B, electrical activating energy can be applied by applying an activating bias arrangement comprising one or more pulses applied across the metal-oxide memory element 140. Bias circuitry such as supply voltages and/or current sources can be formed on the same integrated circuit device and coupled to the top and bottom electrodes 120, 110 for applying the activating bias arrangement to the memory element 140. In alternative embodiments, the activating bias arrangement may be applied using equipment in the manufacturing line that connects to the integrated circuit during manufacturing. In yet other alternative embodiments, the activating bias arrangement can be applied by the user after the manufacturing of the integrated circuit.

As discussed below with reference to FIGS. 14 to 15, thermal activating energy can be applied by performing an activating anneal process.

Referring back to FIG. 2, reading or writing to the memory cell 100 can be achieved by applying appropriate bias arrangements across the memory element 140 to induce a current through the memory element 140. The bias arrangements may each comprise one or more pulses applied across the memory element 140 by applying pulses to one or both of the top and bottom electrodes 120, 110, and the levels and durations of the pulses can be determined empirically for each embodiment. The one or more pulses applied is dependent upon the operation performed, e.g. a reading operation or a programming operation.

The bias arrangements may include pulses having a positive voltage from the top electrode 120 to the bottom electrode 110 (referred to herein as a positive voltage across the memory element 140), and/or may include pulses having a negative voltage from the top electrode 120 to the bottom electrode 110 (referred to herein as a negative voltage across the memory element 140). The resistance of the metal-oxide depends on the applied power or energy, and thus the pulse voltage height and pulse width applied across the memory element 140 determine the resistance of the tungsten-oxide.

In a read (or sense) operation of the data value stored in the memory cell 100, bias circuitry (See, for example, bias circuitry voltage & current sources 1336 of FIG. 13) coupled to the top and bottom electrodes 120, 110 applies bias arrangements across the memory element 140 of suitable amplitude and duration to induce current to flow which does not result in the memory element 140 undergoing a change in resistive state. The current in the memory element 140 is dependent upon the resistance of the memory element 140 and thus the data value stored in the memory cell 100.

In a program operation of a data value to be stored in the memory cell 100, bias circuitry (See, for example, bias circuitry voltage & current sources 1336 of FIG. 13) coupled to the top and bottom electrodes 120, 110 applies bias arrangements across the memory element 140 sufficient to induce a programmable change in the resistance state of memory element 140 to store the data value in the memory cell 100, the resistance of the memory element 140 corresponding to the data value stored in the memory cell 100.

FIGS. 4 and 5A-5C conceptually illustrate the resistive state change behavior of the metal-oxide memory element 140 along with an embodiment of applying an activating bias arrangement as described herein. It will be understood that the pulses shown in FIGS. 5A-5C are simplified and not necessarily to scale.

Figure 4:
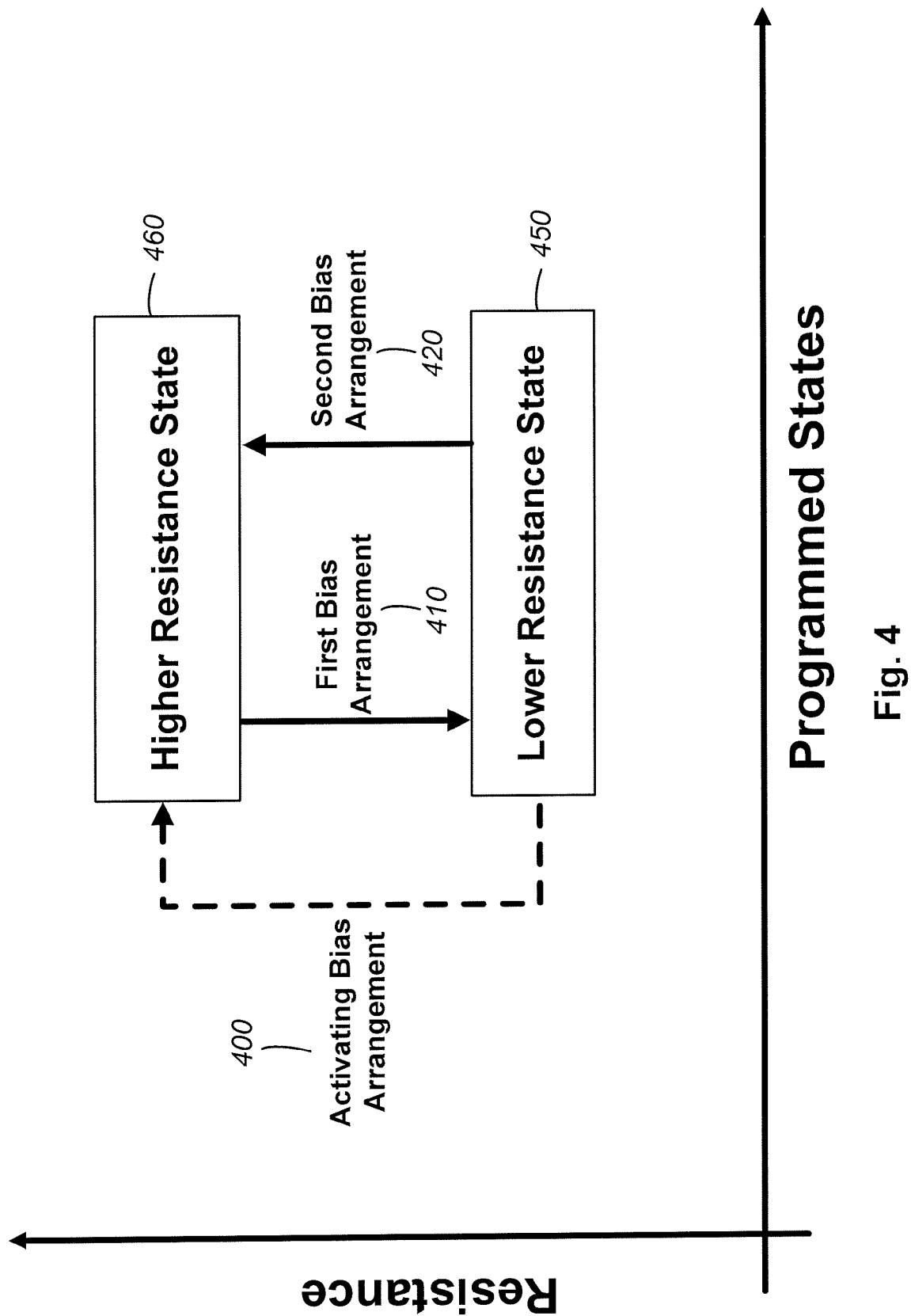

In FIG. 4 the memory element 140 is programmable to a lower resistance state 450 and a higher resistance state 460. More generally the memory element 140 can be programmable to a plurality of resistance states, and can include one or more additional programmed states.

Each of the programmed states correspond to non-overlapping resistance ranges for the memory element 140, and thus the data value stored can be determined by determining which resistance state the memory element 140 is within. In FIG. 4 the lower resistance state 450 is the lowest resistance state used to represent data in the memory element 140, and the higher resistance state 460 is the highest resistance state used to represent data in the memory element 140.

As represented by the arrows of FIG. 4, the operation of FIG. 4 involves first applying an activating bias arrangement 400 across the memory element 140 to induce a resistive change in the memory element 140 from the lower resistance state 450 to the higher resistance state 460. The activating bias arrangement 400 induces current to flow through the metal-oxide memory element 140 and provides a first amount of energy to the memory element 140. As will be discussed in more detail below, the activating bias arrangement 400 need only be applied once (but is not limited to being applied only once), can be determined empirically, activates the metal-oxide memory element 140, and results in the ability to then use relatively low energy bias arrangements to change between the highest and lowest resistance states.

After applying the activating bias arrangement 400, programming bias arrangements are applied across the memory element 140 to change the resistance state of the memory element between the lower and higher resistance states 450, 460. The programming bias arrangements include a first bias arrangement 410 to induce current through the memory element 140 and change the resistance state from the higher resistance state 460 to the lower resistance state 450. The programming bias arrangements include a second bias arrangement 420 to change the resistance state from the lower resistance state 450 to the higher resistance state 460. Because the activating bias arrangement 400 activates the metal-oxide memory element 140, the second bias arrangement 420 induces current to flow through the metal-oxide memory element 140 and provides a second amount of energy that can be less than the first amount of energy to the memory element 140.

In the illustrated embodiments of FIG. 5A-5C, the activating bias arrangement 400 comprises a single pulse having a pulse height of $V_{ACTIVATE}$ and a pulse width 500 applied across the memory element 140, the first bias arrangement 410 comprises a single pulse having a pulse height of $V_{BIAS1}$ and a pulse width 510 applied across the memory element 140, and the second bias arrangement comprises a single pulse having a pulse height of $V_{BIAS2}$ and a pulse width 520 applied across the memory element 140. However, it will be understood that other bias arrangements can alternatively be used. More generally, the bias arrangements may each comprise one or more pulses applied across the memory element 140. The number of pulses and the pulse shapes, including the pulse heights, voltage polarities across the memory element 140, and pulse widths, of each of the bias arrangements can be determined empirically for each embodiment.

FIGS. 5D-5F illustrate a second embodiment using a unipolar operation. In FIGS. 5D-5F, the activating bias arrangement 400 comprises a single pulse having a pulse height of $V_{ACTIVATE}$ and a pulse width of 530 applied across the memory element 140, the first bias arrangement 410 comprises a single pulse having a pulse height of $V_{BIAS}$ and a pulse width 540 across the memory element 140, and the second bias arrangement 420 comprises a single pulse having a pulse height of $V_{BIAS}$ and a pulse width of 550 applied across the memory element 140. As can be seen in FIGS. 5D-5F, the pulse width 450 is less than the pulse width 440.

In embodiments in which the memory element 140 includes an initial resistance state when manufactured which is different from the lower resistance state, the activating bias arrangement may be applied to induce a change from the initial resistance state to the higher resistance state to activate the memory element 140. Alternatively, a bias arrangement may be applied to first change from the initial resistance state to the lower resistance state.

Figure 6:
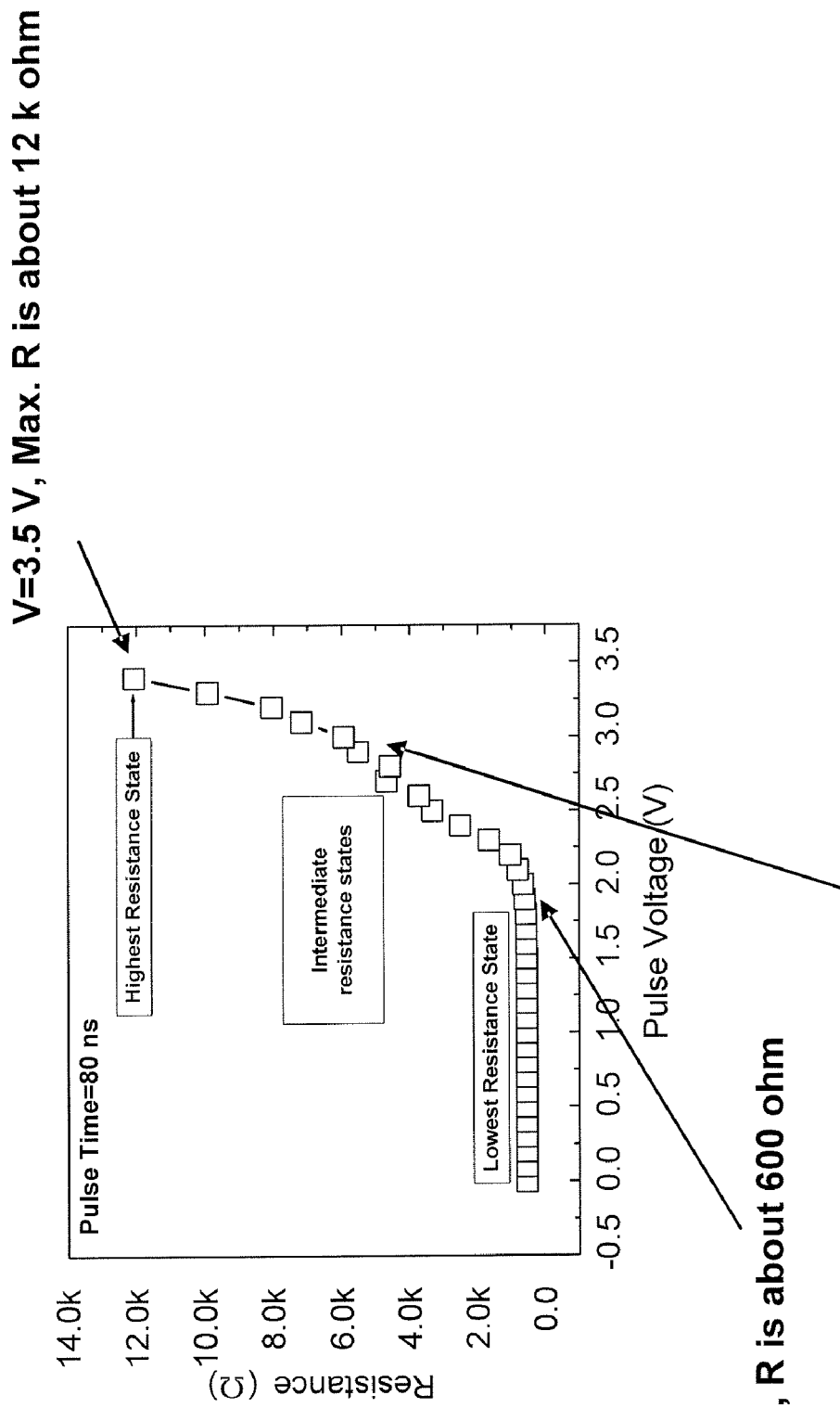
FIG. 6 is measured results of the resistance of a tungsten-oxide memory element of the memory cell structure of FIG. 2.

FIG. 6 is measured results of the resistance of a tungsten-oxide memory element 140 of the memory cell structure of FIG. 2 which can be used to empirically determine an appropriate activating bias arrangement. The tungsten-oxide memory element of the data shown herein was formed by down-stream plasma oxidation following a back-end-of-line W-plug process of depositing W material within a via and performing a CMP process, resulting in the memory element located between the W plug and the subsequently formed top electrode. The process used to form the tungsten-oxide memory element was by down-stream plasma oxidation at 150° C. for 400 sec with an $O_2:N_2$ ratio of 20.

FIG. 6 shows the measured dependence of the resistance of the memory element 140 on the pulse voltage height with a pulse width of 80 ns and rise and fall times of 5 ns respectively. Although not illustrated in the plot of FIG. 6, applying pulses of greater than 3.5 V with a pulse width of 80 ns results in an abrupt decrease in the resistance and a disappearance in the resistive switching behavior of the memory element. Thus, for a pulse width of 80 ns the highest obtainable resistance of the memory element 140 is achieved using a 3.5 V pulse height.

The activation process described herein for the tungsten-oxide memory element 140 can comprise applying an activating bias arrangement to provide a first amount of energy to the memory element to change the resistance state of the memory element 140 from the lowest resistance (initially about 600 ohms in FIG. 5) to the highest obtainable resistance (about 12 k ohms in FIG. 5). Thus, in the illustrated embodiment and the data presented below the activating bias arrangement is selected as a 3.5 V pulse height 80 ns pulse applied across the memory element. However, it will be understood that other activating bias arrangements can alternatively be used. In alternative embodiments, the activating bias arrangement is sufficient to change to a higher resistance state which is not the highest obtainable resistance. For example, the higher resistance state can be an intermediate higher resistance state of FIG. 6 which may be the highest resistance state used to represent data in the memory element 140.

Figure 7A:
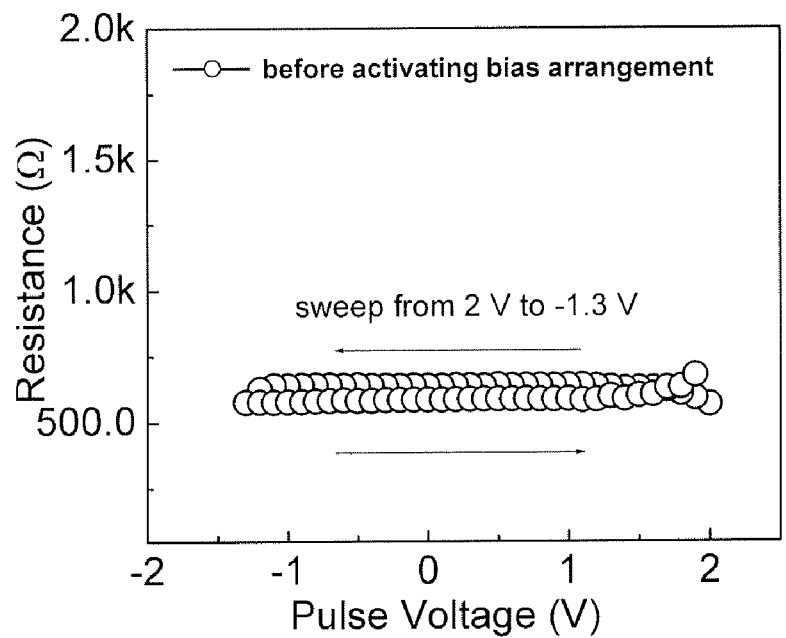
FIGS. 7A-7B are measured results of the resistive switching behavior of tungsten-oxide memory elements before and after applying an activation bias arrangement.
Figure 7B:
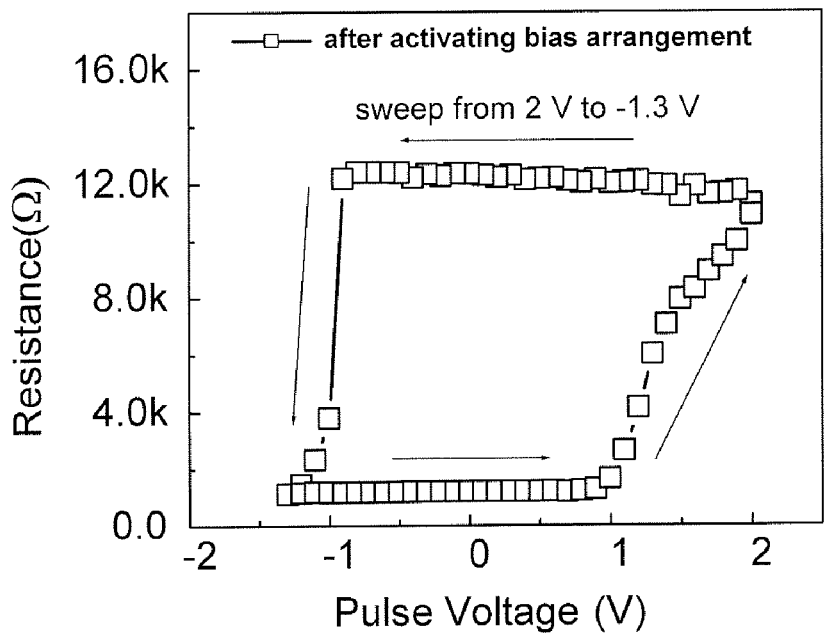

FIGS. 7A and 7B are measured results of the resistive switching behavior of tungsten-oxide memory elements before and after applying an activating bias arrangement comprising a single pulse having a pulse height of 3.5 V and a pulse width of 80 ns across the memory element.

In the data of FIGS. 7A and 7B, pulses having a pulse height from −1.3 V to 2 V and a pulse width of 80 ns are applied across the tungsten-oxide memory element. As can be seen in FIG. 7A, before applying the activating bias arrangement the pulses are insufficient to change the resistance and thus does not exhibit any resistive switching behavior and the resistance stays in the lower resistance state (about 600 ohms).

After applying the activating bias arrangement of a single pulse having a pulse height of 3.5 V and a pulse width of 80 ns, FIG. 7B shows that the memory element exhibits resistive switching behavior using the same pulse voltages and pulse widths used in the data of FIG. 7A. These results show that applying the activating bias arrangement activates the tungsten-oxide material and results in the ability to then use lower voltages to change between the higher and lower resistance states.

Figure 8A:
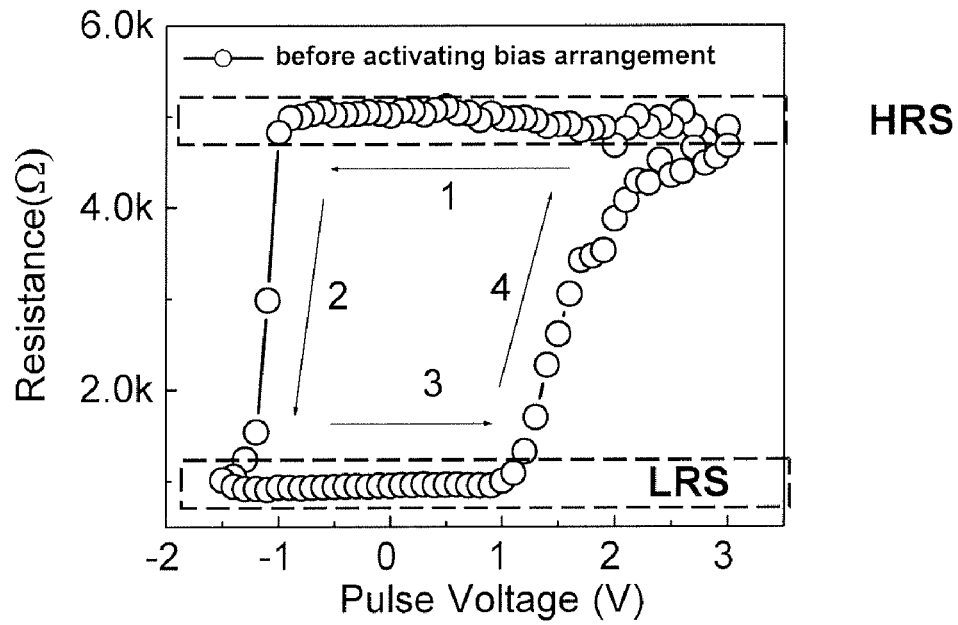
FIGS. 8A-8B are measured results of the resistive switching behavior of tungsten-oxide memory elements before and after applying an activation bias arrangement.
Figure 8B:
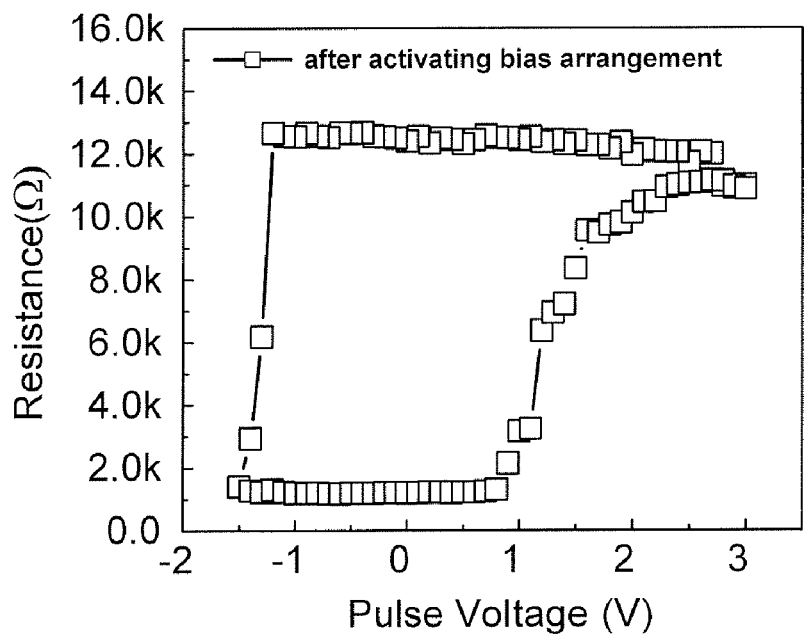

FIGS. 8A-8B are measured results of the resistive switching behavior of tungsten-oxide memory elements using pulses having a pulse height of between 3 V and −1.5 V and a pulse width of 80 ns across the memory element. As can be seen in FIG. 8A, using pulses having a pulse height of between 3 V and −1.5 V results in a shallow resistance window between 5 k ohm and 1 k ohm in the high and low resistance states (HRS and LRS).

After applying the activating bias arrangement of a single pulse having a pulse height of 3.5 V and a pulse width of 80 ns, FIG. 8B shows that the highest resistance of the memory element can subsequently be increased by nearly 2.5 times to 12 k ohms using the same pulse voltages and pulse widths used in the data of FIG. 7A.

Although higher voltages applied to the non-activated device of FIG. 8A may initially result in a higher resistance than 5 k ohm, these higher voltages will also simultaneously exert a large electrical stress on the device which can ultimately damage and cause failure of the device. Since the device after applying the activation bias arrangement can subsequently obtain a resistance of 12 k ohm using a 3 V voltage pulse, applying the activating bias arrangement efficiently increases the resistance of the higher resistance state and also reduces the subsequent electrical stress on the device since lower pulse voltages can then be used for programming.

Figure 9:
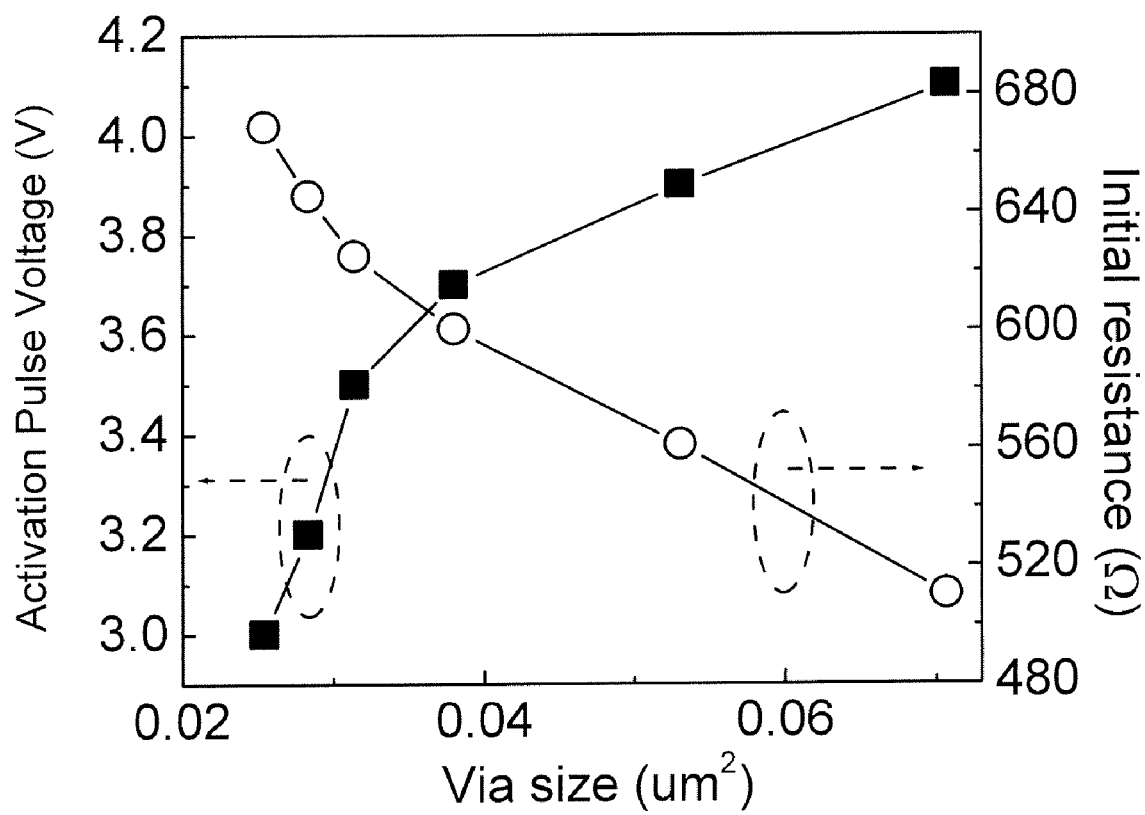
FIG. 9 is measured results of the activation pulse voltage of a single pulse as a function of the cross-sectional size of the tungsten-plug in which the tungsten-oxide memory element is formed.

FIG. 9 is measured results of the activation pulse voltage of a single pulse as a function of the cross-sectional size of the tungsten plug in which the tungsten-oxide memory element is formed. The data shown in FIG. 9 is for a pulse time of 80 ns and was obtained for each device by switching the device to the maximum obtainable resistance. The maximum obtainable resistance for the different sized devices may have slight differences (for example below 1 k ohm difference), but as can be seen in the Figure the activation pulse voltage decreases significantly with smaller size which implies the possibility for further scaling down. The activation pulse voltage of a device is dependent upon the pulse width used, and it has been observed that a longer pulse width often needs a larger pulse voltage.

Figures 10A, 10B:
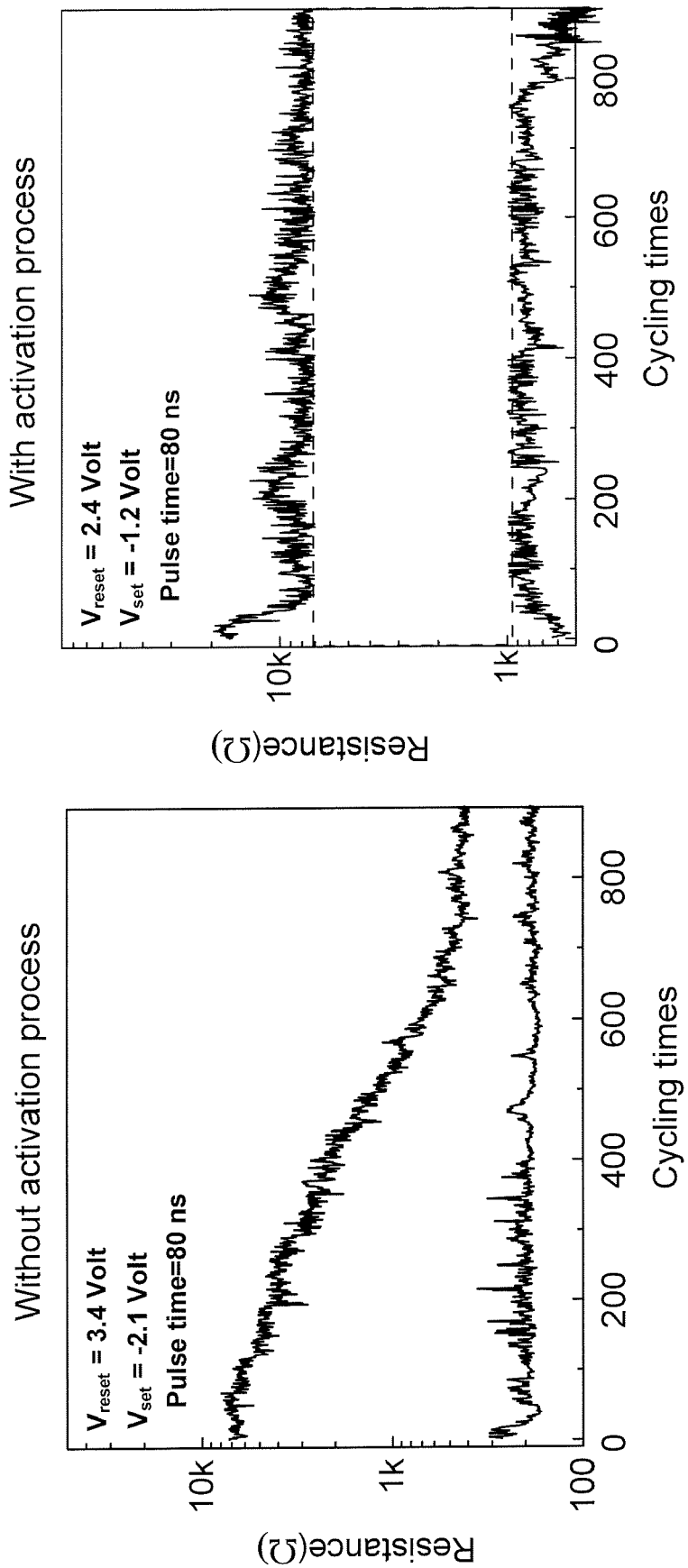
FIGS. 10A and 10B respectively illustrate cycling endurance measurements on tungsten-oxide memory elements without and with the activating process.

FIGS. 10A and 10B respectively illustrate cycling endurance measurements on tungsten-oxide memory elements without and with the activation process of applying an activating bias arrangement as described herein.

FIG. 10A is a plot of measured data of the resistance of the tungsten-oxide memory element versus cycle time without the activation process. In the data of FIG. 10A a pulse of 3.4V/80 ns is used to induce a resistive change from the lower resistance state 350 to the higher resistance state 360, and using a pulse of −2.1 V/80 ns across the memory element to induce a change from the higher resistance state 360 to the lower resistance state 350.

As can be seen in FIG. 10A, the device without the activation process shows unstable cycling results and a significant degradation in the resistance of the higher resistance state with cycling. It is believed that the degradation is due to the electrical stress on the tungsten-oxide material caused by the large voltage magnitude used to induce a resistive change from the lower resistance state 450 to the higher resistance state 460.

Applying the activating bias arrangement of a single pulse having a pulse height of 3.5V and a pulse width of 80 ns, FIG. 10B shows the measured cycling endurance of a tungsten-oxide memory element. As can be seen by comparing FIG. 10B with FIG. 10A, the resistance of the higher resistance state and the resistive window between the higher and lower resistance state are increased and stable with cycling. The voltage magnitudes of the data of FIG. 9B ($V_{reset}$=2.4 V/80 ns, $V_{set}$=−1.2 V/80 ns) are also smaller than the voltage magnitudes of the data of FIG. 9A ($V_{reset}$=3.4 V/80 ns, $V_{set}$=−2.1 V/80 ns).

Figure 11A:
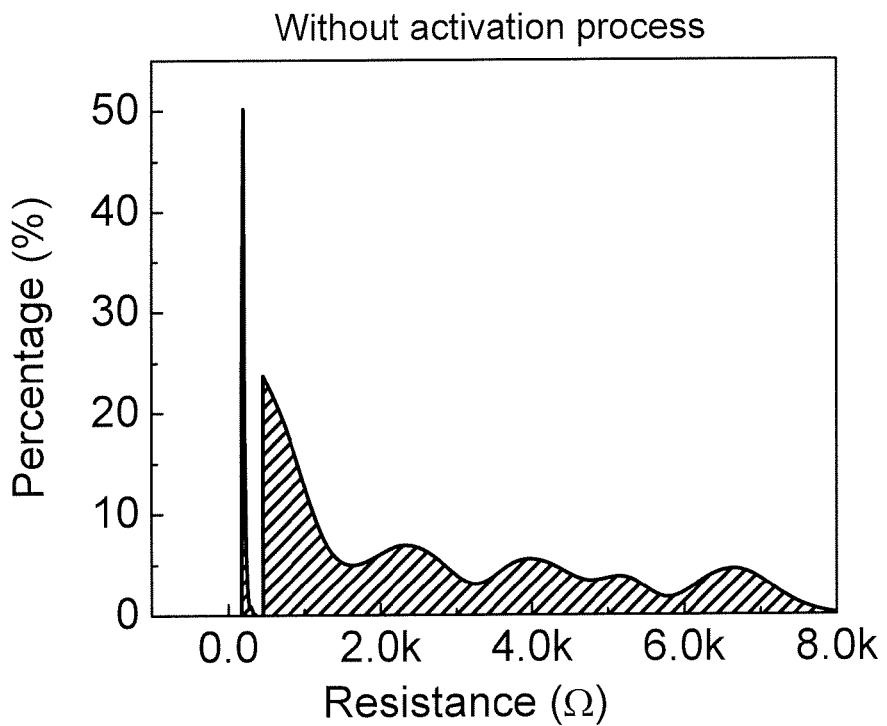
FIGS. 11A and 11B illustrate the resistance distribution of the higher and lower resistance states for the data of FIGS. 10A and 10B respectively.
Figure 11B:
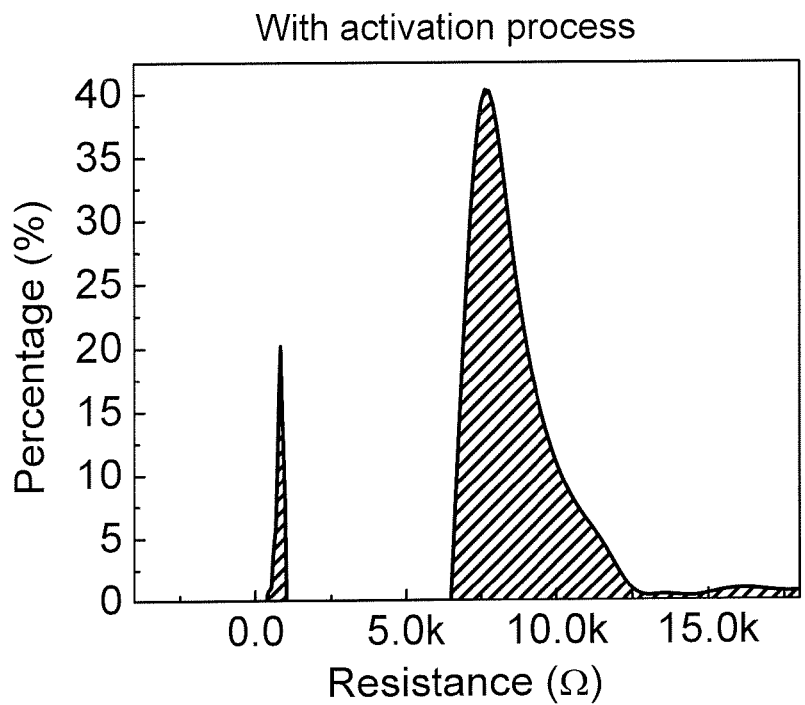

FIGS. 11A and 11B illustrate the resistance distribution of the higher and lower resistance states for the data of FIGS. 11A and 11B respectively.

As can be seen in the data of FIGS. 10A-10B and 11A-11B, the activation process results in a significant improvement in the distribution in the higher resistance state, the higher resistance state is more stable with cycling, and the ratio of the higher resistance state to lower resistance state is nearly 10 and thus the activation process increases the resistive window. These results demonstrate that the activation process efficiently improves the switching stability and performance of tungsten-oxide based RRAM.

FIGS. 10A-10B and 11A-11B shows that both devices have distributions in the higher resistance state wider than those in the lower resistance state. The wider higher resistance state may be due to the different amount of leakage path remaining in the tungsten-oxide material during the switching cycles.

Figures 12A, 12B:
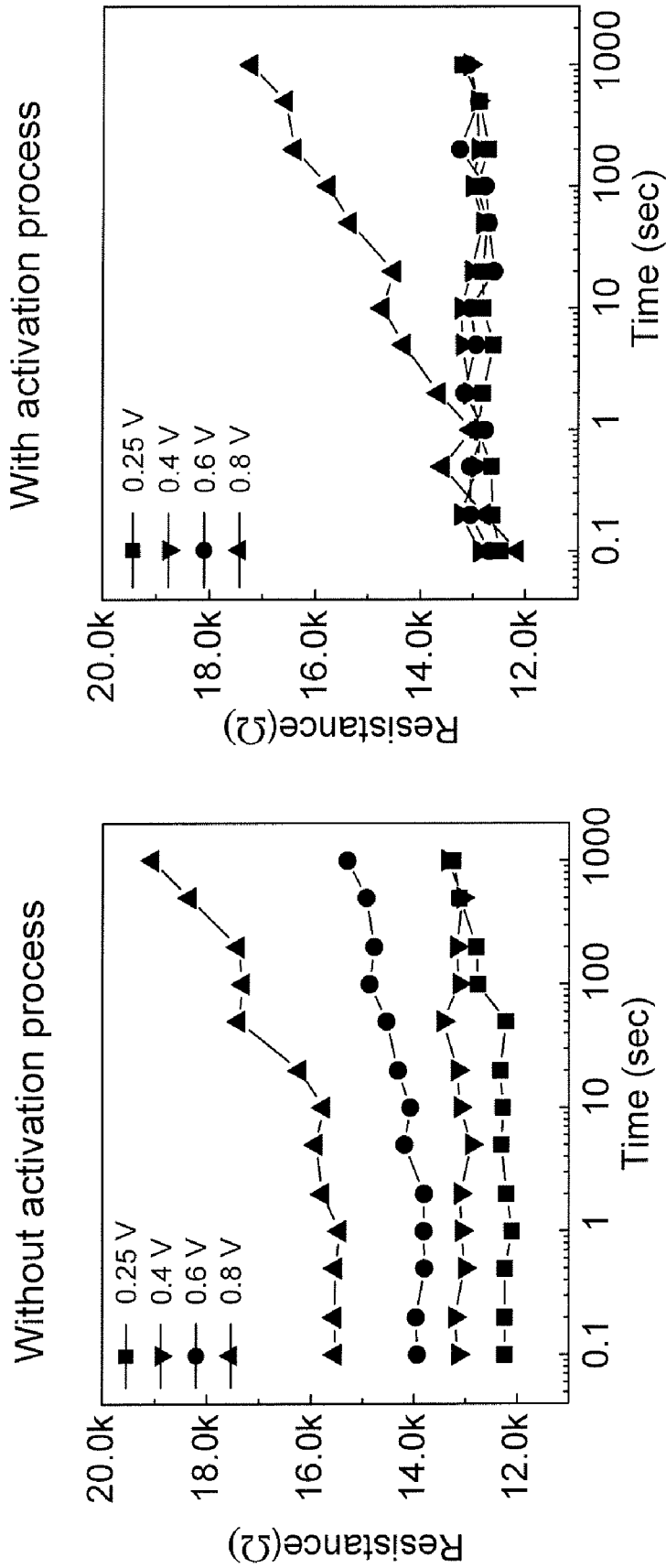
FIGS. 12A and 12B show the measured read disturb results in the higher resistance state for devices without and with the activating process respectively.

FIGS. 12A and 12B show the measured read disturb results in the higher resistance state for devices without and with the activation process respectively of a single pulse having a pulse height of 3.5V and a pulse width of 80 ns. As can be seen in FIG. 12B, the device having the activation process has excellent immunity to read disturb below 0.6 V, showing that the activating process can efficiently improve the read disturbance of the higher resistance state.

Figure 13B:
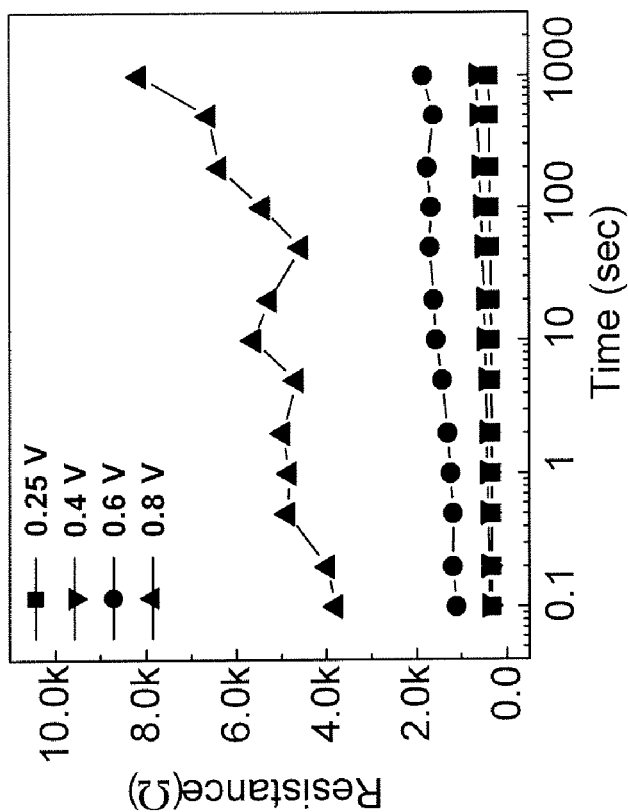
FIGS. 13A and 13B show the measured read disturb results in the lower resistance state for devices without and with the activating process respectively.
Figure 13A:
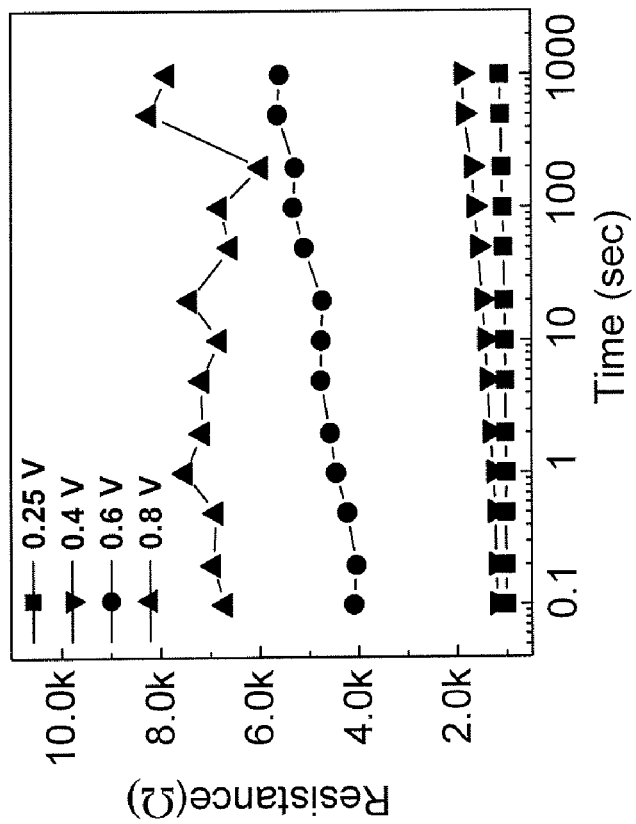

FIGS. 13A and 13B show the measured read disturb results in the lower resistance state for devices without and with the activation process. As can be seen in FIG. 13B, the device having the activation process has excellent immunity to read disturb below 0.6 V, showing that the activation process can efficiently improve the read disturbance of the lower resistance state. These results all show poor behavior at 0.8 V, which is reasonable because the voltage is close to that used to switch between the lower resistance state and the higher resistance state.

Using the activating bias arrangement described herein results in the ability to subsequently use lower energy bias arrangements for programming the tungsten-oxide memory element. The activating bias arrangement is also shown to result in improved resistive switching performance of the tungsten-oxide material including improved cycle endurance and improved read disturbance performance. Additionally, the activating bias arrangement is shown to result in a larger resistance window between the lower and higher and resistance states, thereby providing an opportunity for multi-bit operation.

In the method described above with respect to FIGS. 4-13B the activation process was carried out by applying an activation bias arrangement 400 to provide the activating energy to the metal-oxide memory element 140. FIG. 14 illustrates the resistive state change behavior of the metal-oxide memory element 140 along with an embodiment of applying an activating anneal process 1400 to activate the memory element 140.

Figure 14:
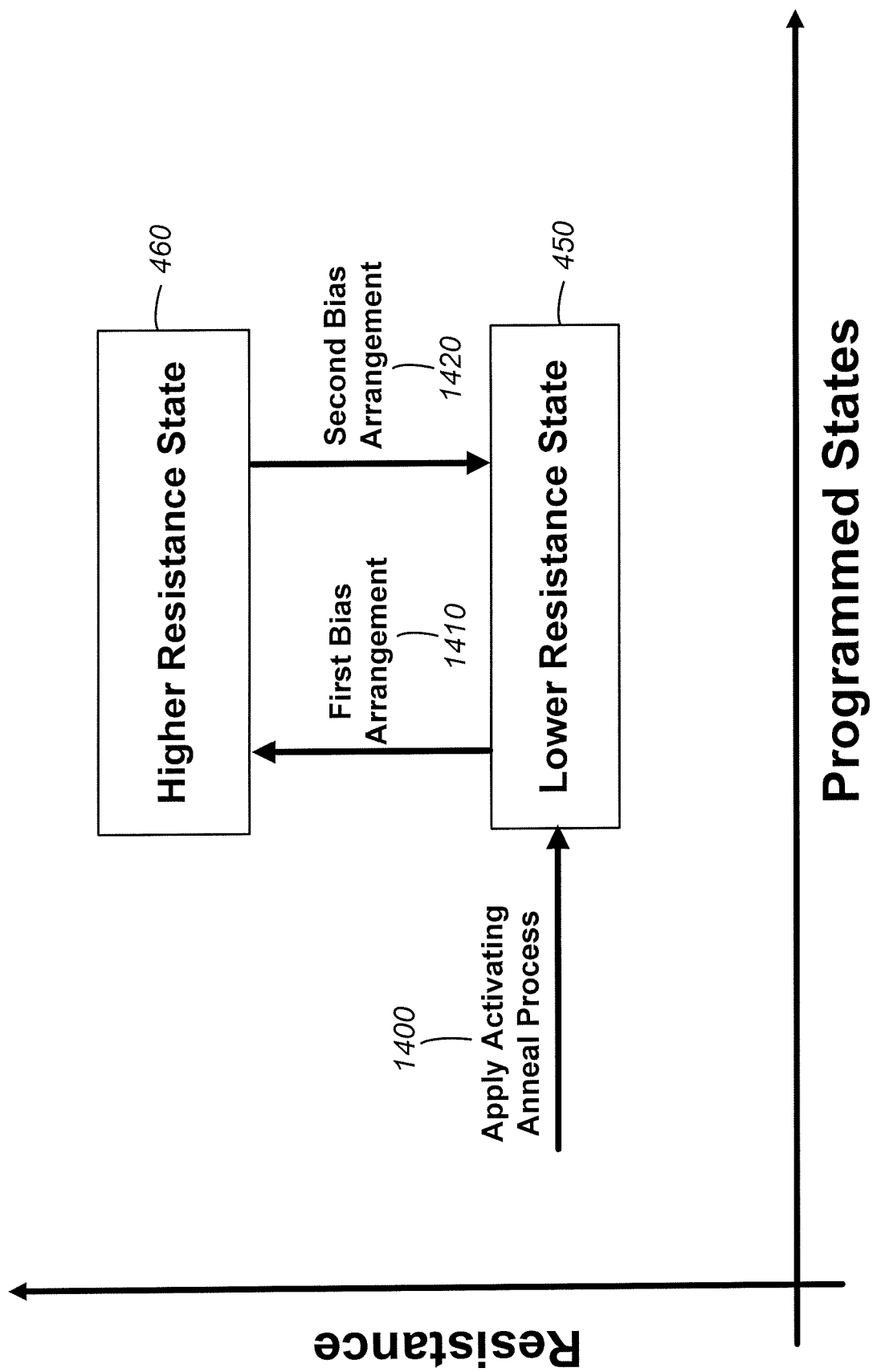
FIG. 14 illustrates the resistive state change behavior of the metal-oxide memory element along with an embodiment of applying an activating anneal process.

As represented by the arrows of FIG. 14, following formation of the metal-oxide memory element 140 an activating anneal process 1400 is performed to provide thermal activating energy to the memory element 140. The activating anneal process removes unnecessary leakage paths inside the metal-oxide material and causes an increase in the resistance of the memory element 140 from an initial resistance of the memory element 140 as formed. However, as represented by the arrows of FIG. 14, the memory element 140 is still in the lower resistance state following the activating anneal process.

After applying the activating anneal process 1400, programming bias arrangements are applied across the memory element 140 to change the resistance state of the memory element between the lower and higher resistance states 450, 460. The programming bias arrangements include a first bias arrangement 1410 to induce current through the memory element 140 and change the resistance state from the lower resistance state 450 to the higher resistance state 460. The first bias arrangement 1410 may be for, example, any of the bias arrangements discussed above with reference to the bias arrangement 420 of FIG. 4. The programming bias arrangements include a second bias arrangement 1420 to change the resistance state from the higher resistance state 460 to the lower resistance state 450. The second bias arrangement 1420 may be for, example, any of the bias arrangements discussed above with reference to the bias arrangement 410 of FIG. 4.

The activating anneal process can be carried out using any suitable high temperature system including for example, an oven or a rapid thermal annealing (RTA) system. The time and temperature of the activating anneal process will depend upon a number of factors, and will vary from embodiment to embodiment. For example, the temperature can range from 100 degrees C. to 400 degrees C. with a time of 10 minutes to 60 minutes. The activating anneal process may be carried out, for example, during any of various stages in the manufacturing process of an integrated circuits containing the metal-oxide memory elements. For example, the activating anneal process may be carried out prior to formation of other circuitry such as bias circuitry formed on the same integrated circuit. As another example, the activating anneal process can be performed after the formation of the other circuitry on the integrated circuit.

The activating anneal process need only be applied once (but is not limited to being applied only once), activates the metal-oxide memory element 140, and results in the ability to then use relatively low energy bias arrangements to change between the higher and lower resistance states.

Figure 15:
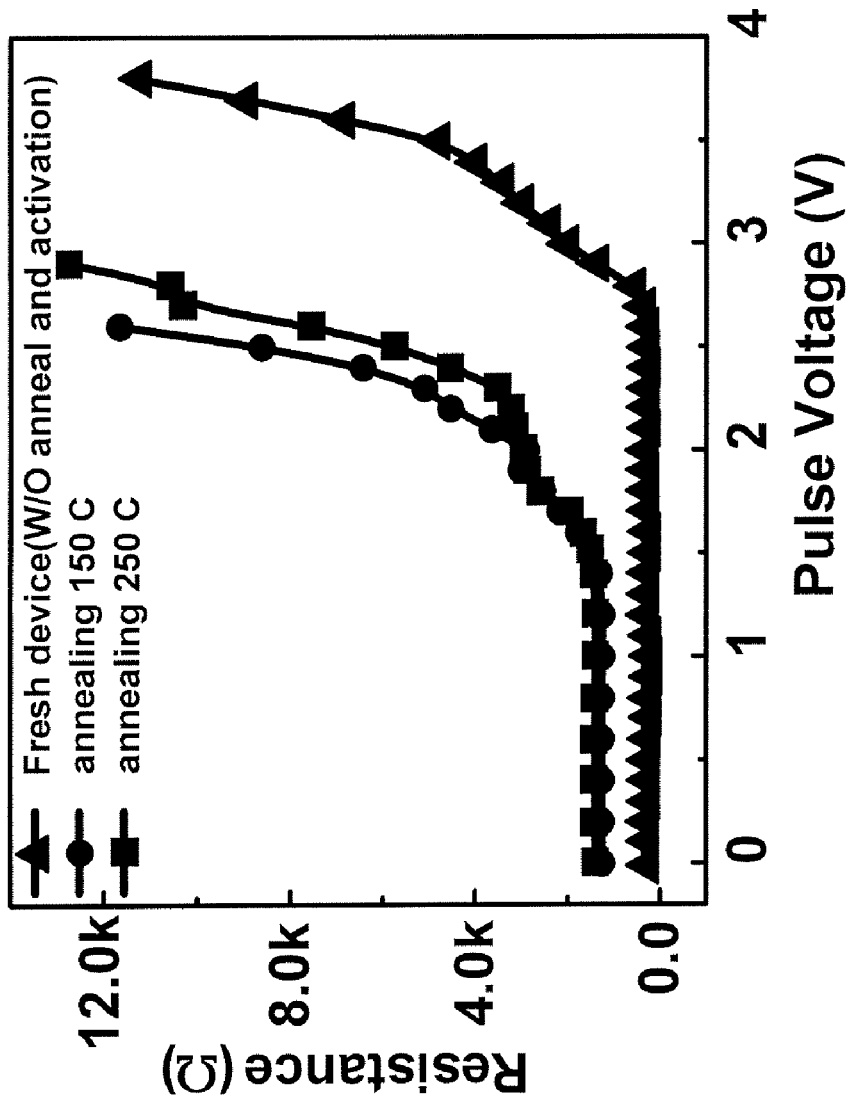
FIG. 15 is measured results of the resistance of metal-oxide memory elements versus pulse voltage with and without the activation process of performing the activating anneal process.

FIG. 15 is a plot of measured data of the resistance of tungsten-oxide memory elements versus pulse voltage using a pulse width of 80 ns with and without performing the activating anneal process as described herein. As can be seen in FIG. 15, the device without the activating anneal process has an initial resistance of about 600 ohms and requires a voltage pulse of 3.7 V to achieve a resistance of about 12 k ohm. FIG. 15 also shows the measured resistance of devices after annealing at 150° C. for 10 minutes and 250° C. for 10 minutes respectively. As can be seen, after the annealing process the initial resistance is increased and the resistance can be changed to the high resistance using voltages of as little as 2.7 Volts.

In the activation process discussed above with respect to FIG. 14, activating was achieved by performing the activating anneal process 1400. In alternative embodiments, the activation process includes both the activating anneal process 1400 and an activating bias arrangement such as that discussed above with respect to FIG. 4.

The activating methods described herein have been demonstrated for tungsten-oxide memory elements. However, as described below the methods may be extended to other metal-oxides such as nickel oxide, aluminum oxide, magnesium oxide, cobalt oxide, titanium oxide, titanium-nickel oxide, zirconium oxide, and copper oxide. It is theorized that the resistive behavior of tungsten-oxide as well as other metal-oxides may be due to the rupture and formation of filaments (a filament may be composed of ions or vacancies), and that the number of remaining filaments determines the resistance of the tungsten-oxide. The methods described herein of applying an activating process to activate the metal-oxide can terminate unnecessary leakage paths inside the metal-oxide material. Thus, the operating voltages for programming the metal-oxide memory element are reduced, thereby reducing the electrical stress on the memory element. Thus, the methods described herein may be extended to other metal-oxides which may be characterized by resistance switching behavior which depends upon the rupture and formation of filaments.

Figure 16:
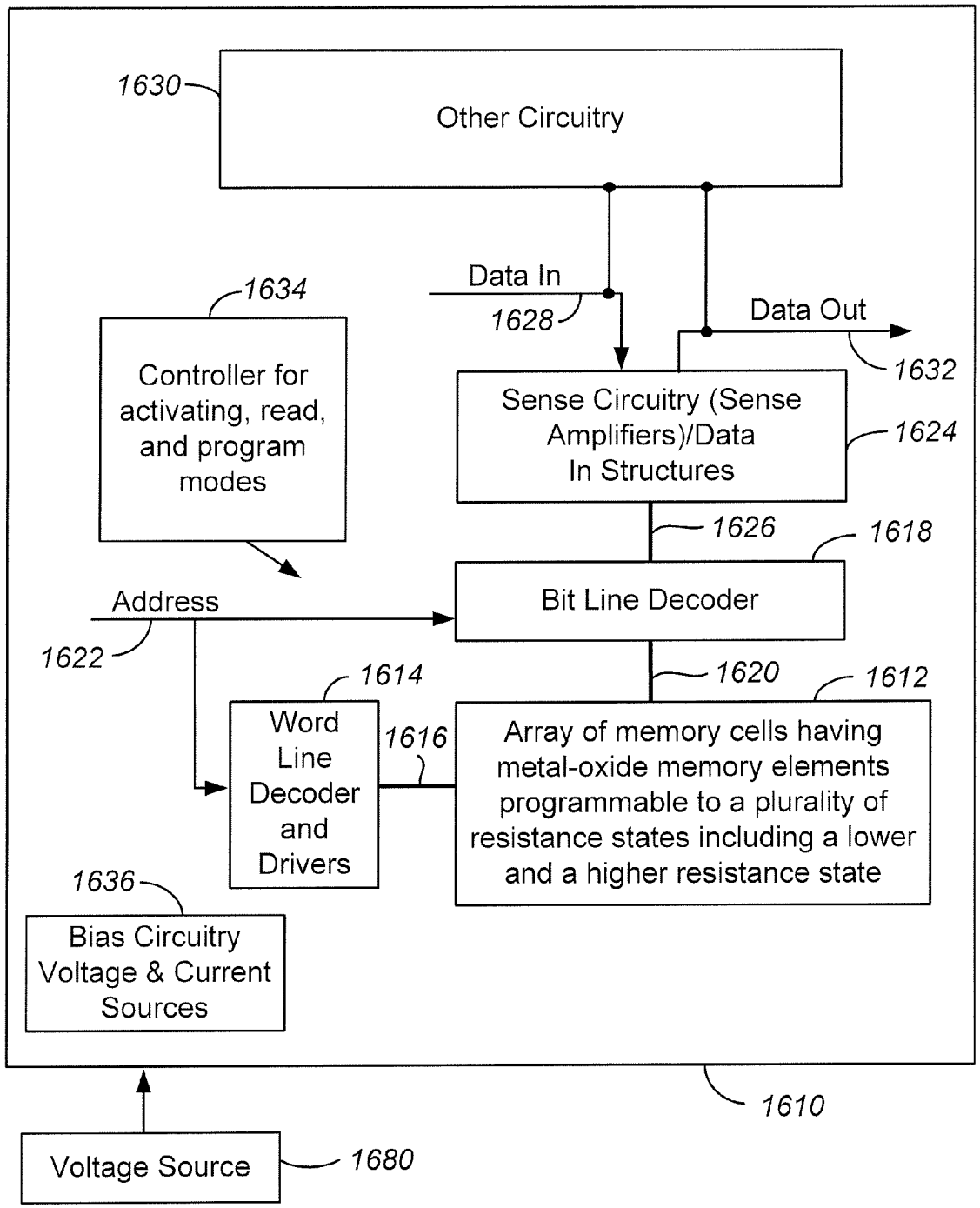
FIG. 16 is a simplified block diagram of an integrated circuit in which the operations for switching the resistance of tungsten-oxide memory elements as described herein can be implemented.

FIG. 16 is a simplified block diagram of an integrated circuit 1610 in which the operations for switching the resistance of metal-oxide memory elements as described herein can be implemented. The integrated circuit 1610 includes a memory array 1612 of memory cells having metal-oxide memory elements programmable to a plurality of resistance states including a lower resistance state and a higher resistance state. A word line decoder 1614 having activating, read, and program modes is coupled to and in electrical communication with a plurality of word lines 1616 arranged along rows in the memory array 1612. A bit line (column) decoder 1618 is in electrical communication with a plurality of bit lines 1620 arranged along columns in the array 1612 for activating, reading, and programming the metal-oxide based memory cells (not shown) in array 1612.

Addresses are supplied on bus 1622 to word line decoder and drivers 1614 and bit line decoder 1618. Sense circuitry (Sense amplifiers) and data-in structures in block 1624, including voltage and/or current sources for the activating, read, and program modes are coupled to bit line decoder 1618 via data bus 1626. Data is supplied via a data-in line 1628 from input/output ports on integrated circuit 1610, or from other data sources internal or external to integrated circuit 1610, to data-in structures in block 1624. Other circuitry 1630 may be included on integrated circuit 1610, such as a general purpose processor or special purpose application circuitry, or a combination of modules providing system-on-a-chip functionality supported by array 1612. Data is supplied via a data-out line 1632 from the sense amplifiers in block 1624 to input/output ports on integrated circuit 1610, or to other data destinations internal or external to integrated circuit 1610.

The integrated circuit 1610 includes a controller 1634 for activating, read, and program modes of the memory cells of the array 1612. The controller 1634, implemented in this example using a bias arrangement state machine, controls the application of bias circuitry voltage & current sources 1636 for the application of bias arrangements including activating, read, and program to the word lines 1616, bit lines 1620, and in some embodiments source lines. Controller 1634 may be implemented using special-purpose logic circuitry as known in the art. In alternative embodiments, controller 1634 comprises a general-purpose processor, which may be implemented on the same integrated circuit to execute a computer program to control the operations of the device. In yet other embodiments, a combination of special-purpose logic circuitry and a general-purpose processor may be utilized for implementation of controller 1634.

As shown in FIG. 16, an external voltage source 1680 is coupled to the integrated circuit 1510 to provide a supply voltage for operation of the device. As was described above, the activation process described herein allows for subsequent lower voltage switching operation of the tungsten-oxide memory elements. Thus the voltage source 1680 can be a relatively low voltage. In embodiments the supply voltage of the voltage source 1680 may be greater than or nearly the same as the pulse heights used in programming and also less than the pulse heights used in the activation process. Thus the bias circuitry of block 1636 may include charge pumps for obtaining the higher voltages needed for the activation process. In alternative embodiments, the activation process may be applied using equipment in the manufacturing line that connects to the integrated circuit 1610 during manufacture, such as test equipment, to apply the activating bias arrangement across the metal-oxide memory elements of array 1612.

Figure 17:
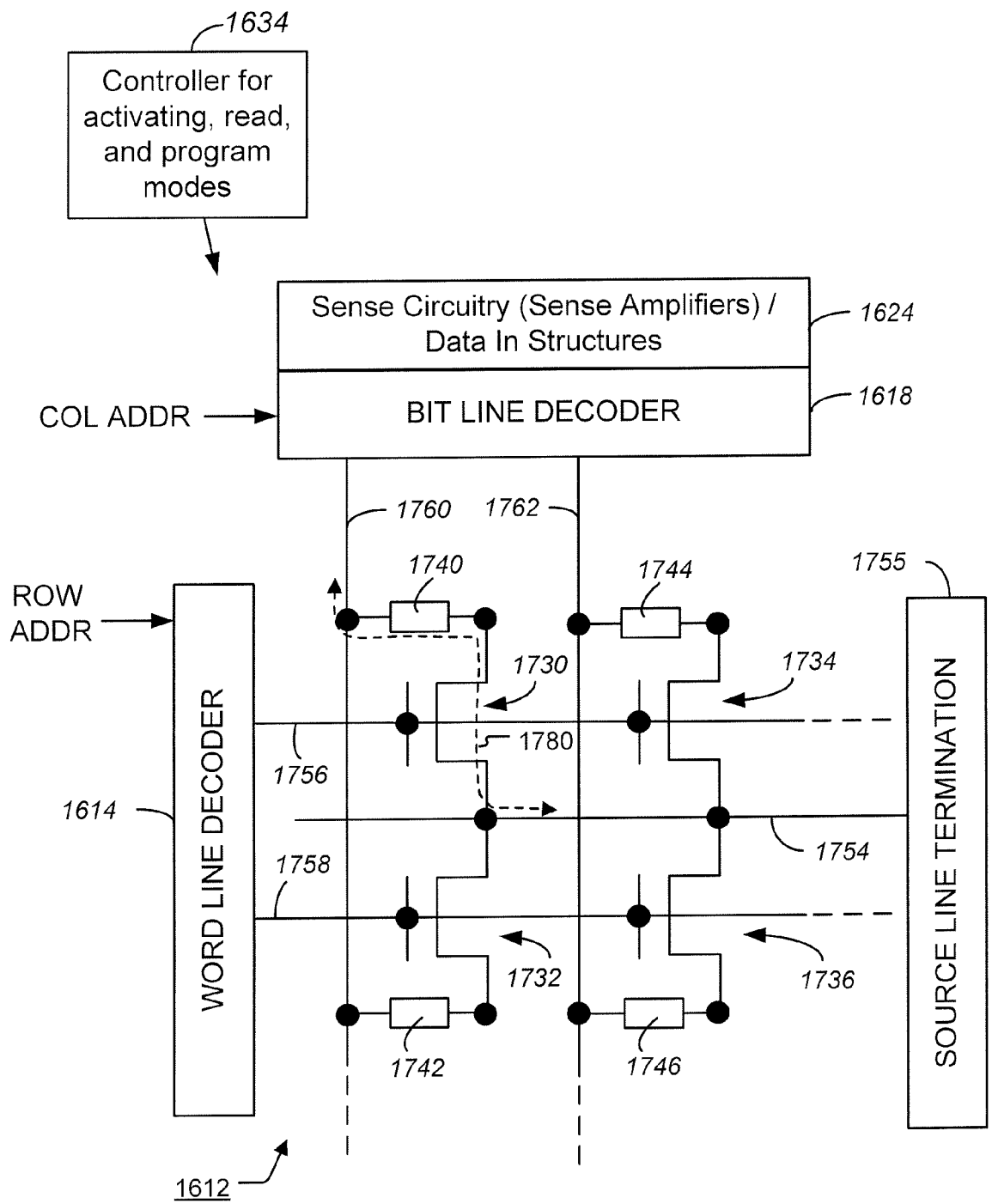
FIG. 17 illustrates a portion of the memory array of FIG. 16.

As shown in FIG. 17, each of the memory cells of array 1612 includes an access transistor (or other access device such as a diode) and a metal-oxide based memory element. In FIG. 17 four memory cells 1730, 1732, 1734, 1736 having respective memory elements 1740, 1742, 1744, 1746 are illustrated, representing a small section of an array that can include millions of memory cells. The memory elements are programmable to a plurality of resistance states including a lower and a higher resistance state.

Sources of each of the access transistors of memory cells 1730, 1732, 1734, 1736 are connected in common to source line 1754 that terminates in source line termination circuit 1755, such as a ground terminal. In another embodiment the source lines of the access devices are not electrically connected, but independently controllable. The source line termination circuit 1755 may include bias circuitry such as voltage sources and current sources, and decoding circuits for applying bias arrangements, other than ground, to the source line 1754 in some embodiments.

A plurality of word lines including word lines 1756, 1758 extend in parallel along a first direction. Word lines 1756, 1758 are in electrical communication with word line decoder 1614. The gates of access transistors of memory cells 1730 and 1734 are connected to word line 1756, and the gates of access transistors of memory cells 1732 and 1736 are connected in common to word line 1758.

A plurality of bit lines including bit lines 1760, 1762 extend in parallel in a second direction and are in electrical communication with bit line decoder 1618. In the illustrated embodiment each of the memory elements are arranged between the drain of the corresponding access device and the corresponding bit line. Alternatively, the memory elements may be on the source side of the corresponding access device.

It will be understood that the memory array 1612 is not limited to the array configuration illustrated in FIG. 17, and additional array configurations can also be used. Additionally, instead of MOS transistors, bipolar transistors or diodes may be used as access devices in some embodiments.

In operation each of the memory cells in the array 1612 store data depending upon the resistance of the corresponding memory element. The data value may be determined, for example, by comparison of current on a bit line for a selected memory cell to that of a suitable reference current by sense amplifiers of sense circuitry 1624. The reference current can be established to that a predetermined range of currents correspond to a logical "0", and a differing range of currents correspond to a logical "1". In a memory cell having three or more states, reference currents can be established so that differing ranges of bit line currents correspond to each of the three or more states.

Activating, reading, or writing to a memory cell of array 1612 can be achieved by applying a suitable voltage to one of word lines 1756, 1758 and coupling one of bit lines 1760, 1762 to a voltage so that current flows through the selected memory cell. For example, a current path 1780 through a selected memory cell (in this example memory cell 1730 and corresponding memory element 1740) is established by applying voltages to the bit line 1760, word line 1756, and source line 1754 sufficient to turn on the access transistor of memory cell 1730 and current in path 1780 to flow from the bit line 1760 to the source line 1754, or vice-versa. The level and duration of the voltages applied is dependent upon the operation performed.

In an activation operation of the memory element 1740 of memory cell 1730, bias circuitry (See, for example, bias circuitry voltage & current sources 1636 of FIG. 16) coupled to the array 1612 applies an activating bias arrangement as described herein comprising one or more pulses to the bit line 1760 and/or word line 1756 and/or source line 1754 to induce current in path 1780. The resultant pulses across the memory element 1740 provides the activating energy to the memory element 1740 to change the resistance state of the memory element 1740 from the lower resistance state to the higher resistance state. In an alternative activation process, the pulses may be applied using equipment in the manufacturing line that connects to the chips during manufacture, such as test equipment.

After the activation operation, reading and writing to the memory cell 1730 can be achieved by applying suitable voltages to word line 1756, bit line 1760, and source line 1754 so that current flows in path 1780.

In a read (or sense) operation of memory cell 1730, word line decoder 1614 facilitates providing word line 1756 with a suitable voltage to turn on the access transistor of the memory cell 1730. Bit line decoder 1618 facilitates supplying a voltage to bit line 1760 of suitable amplitude and duration to induce current in path 1780 that does not result in the memory element 1740 undergoing a change in resistive state. The current on the bit line 1760 and through the memory element 1730 is dependent upon the resistance of the memory element 1740 and thus the data value stored in the memory cell 1730. Thus, the data value stored in the memory cell 1730 may be determined, for example, by comparison of the current on bit line 1760 with a suitable reference current by sense amplifiers of sense circuitry 1624.

In a program operation of a data value to be stored in the memory cell 1730, bias circuitry (See, for example bias circuitry voltage & current sources 1636 of FIG. 16) coupled to the array 1612 applies programming bias arrangements as described herein comprising one or more pulses to the bit line 1760 and/or word line 1756 and/or source line 1754 to induce current in path 1780. The resultant pulses across the memory element 1740 change the resistance state of the memory element 1740 between the plurality of resistance states including between the lower resistance state to the higher resistance state.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A method for manufacturing a memory device, the method comprising:
   forming a metal-oxide memory element;
   after said forming, applying an activating energy to the metal-oxide memory element and
   forming bias circuitry coupled to the metal-oxide memory element, the bias circuitry adapted to apply a plurality of bias arrangements across the metal-oxide memory element, the plurality of bias arrangements comprising:
   a first bias arrangement to change a resistance state of the metal-oxide memory element from a higher resistance state to a lower resistance state; and
   a second bias arrangement to change the resistance state of the metal-oxide memory element from the lower resistance state to the higher resistance state.

2. The method of claim 1, wherein:
   the metal-oxide memory element has an initial resistance after said forming; and
   applying the activating energy increases the resistance of the metal-oxide memory element.

3. The method of claim 1, wherein the applying the activating energy comprises performing an activating anneal process.

4. The method of claim 1, wherein:
   the applying the activating energy comprises applying an activating bias arrangement across the metal-oxide memory element to change the resistance state from the lower resistance state to the higher resistance state.

5. The method of claim 4, wherein the higher resistance state is the highest resistance state used to represent data in the metal-oxide memory element.

6. The method of claim 4, wherein the bias circuitry is adapted to apply the activating bias arrangement.

7. The method of claim 4, wherein:
the activating bias arrangement provides a first amount of energy to the metal-oxide memory element; and
the second bias arrangement provides a second amount of energy to the metal-oxide memory element less than the first amount of energy.

8. The method of claim 4, wherein:
the activating bias arrangement comprises a first pulse across the metal-oxide memory element having a pulse width and a pulse height; and
the second bias arrangement comprises a second pulse across the metal-oxide memory element having a pulse width and a pulse height, the pulse height of the second pulse less than the pulse height of the first pulse.

9. The method of claim 8, wherein the first pulse has a voltage polarity across the metal-oxide memory element the same as that of the second pulse.

10. The method of claim 8, wherein the first bias arrangement comprises a third pulse across the metal-oxide memory element having a pulse width and a pulse height, the pulse height of the third pulse less than the pulse height of the first pulse.

11. The method of claim 10, wherein:
the first and second pulses have a first voltage polarity across the metal-oxide memory element; and
the third pulse has a second voltage polarity across the metal-oxide memory element opposite that of the first voltage polarity.

12. The method of claim 10, wherein the first, second and third pulses have the same voltage polarity across the metal-oxide memory element.

13. The method of claim 10, wherein the pulse width of the third pulse is greater than the pulse width of the second pulse.

14. The method of claim 10, wherein the pulse widths of the first, second and third pulses are substantially the same.

15. The method of claim 8, wherein:
the pulse height of the first pulse is greater than a supply voltage coupled to the memory device; and
the pulse height of the second pulse is less than the supply voltage coupled to the memory device.

16. The method of claim 1, wherein the metal-oxide memory element comprises tungsten-oxide.

17. The method of claim 1, wherein the metal-oxide memory element comprises a metal oxide from the group of nickel oxide, aluminum oxide, magnesium oxide, cobalt oxide, titanium oxide, titanium-nickel oxide, zirconium oxide, and copper oxide.

18. A memory device comprising:
a metal-oxide memory element programmable to a plurality of resistance states including a lower resistance state and a higher resistance state; and
bias circuitry adapted to apply bias arrangements across the metal-oxide memory element, the bias arrangements comprising:
an activating bias arrangement to apply an activating energy to the metal-oxide memory element;
a first bias arrangement to change a resistance state of the metal-oxide memory element from a higher resistance state to a lower resistance state; and
a second bias arrangement to change the resistance state of the metal-oxide memory element from the lower resistance state to the higher resistance state.

19. The device of claim 18, wherein the higher resistance state is the highest resistance state used to represent data in the metal-oxide memory element.

20. The device of claim 18, wherein the activating bias arrangement is adapted to change the resistance state of the metal-oxide memory element from the lower resistance state to the higher resistance state.

21. The device of claim 20, wherein:
the activating bias arrangement provides a first amount of energy to the metal-oxide memory element; and
the second bias arrangement provides a second amount of energy to the metal-oxide memory element less than the first amount of energy.

22. The device of claim 20, wherein:
the activating bias arrangement comprises a first pulse across the metal-oxide memory element having a pulse width and a pulse height; and
the second bias arrangement comprises a second pulse across the metal-oxide memory element having a pulse width and a pulse height, the pulse height of the second pulse less than the pulse height of the first pulse.

23. The device of claim 22, wherein the first pulse has a voltage polarity across the metal-oxide memory element the same as that of the second pulse.

24. The device of claim 22, wherein the first bias arrangement comprises a third pulse across the metal-oxide memory element having a pulse width and a pulse height, the pulse height of the third pulse less than the pulse height of the first pulse.

25. The device of claim 24, wherein:
the first and second pulses have a first voltage polarity across the metal-oxide memory element; and
the third pulse has a second voltage polarity across the metal-oxide memory element opposite that of the first voltage polarity.

26. The device of claim 24, wherein the first, second and third pulses have the same voltage polarity across the metal-oxide memory element.

27. The device of claim 24, wherein the pulse width of the third pulse is greater than the pulse width of the second pulse.

28. The device of claim 24, wherein the pulse widths of the first, second and third pulses are substantially the same.

29. The device of claim 22, wherein:
the pulse height of the first pulse is greater than a supply voltage coupled to the memory device; and
the pulse height of the second pulse is less than the supply voltage coupled to the memory device.

30. The device of claim 18, wherein the metal-oxide memory element comprises tungsten-oxide.

31. The device of claim 18, wherein the metal-oxide memory element comprises a metal oxide from the group of nickel oxide, aluminum oxide, magnesium oxide, cobalt oxide, titanium oxide, titanium-nickel oxide, zirconium oxide, and copper oxide.

* * * * *